United States Patent [19]

Gardlik et al.

[11] Patent Number: 5,200,174
[45] Date of Patent: Apr. 6, 1993

[54] GEL STICK ANTIPERSPIRANT COMPOSITION CONTAINING 2-OXAZOLIDINONE DERIVATIVE AND PROCESS FOR MAKING THEM

[75] Inventors: John M. Gardlik; Brian D. Hofrichter, both of Cincinnati, Ohio

[73] Assignee: Procter & Gamble, Cincinnati, Ohio

[21] Appl. No.: 696,375

[22] Filed: May 6, 1991

[51] Int. Cl.$^5$ .......................... A61K 7/32; A61K 7/34; A61K 7/38

[52] U.S. Cl. ................................ 424/66; 424/DIG. 5; 424/68

[58] Field of Search ........................ 424/DIG. 5, 68, 66

[56] References Cited

U.S. PATENT DOCUMENTS

| | | | |
|---|---|---|---|
| 4,720,381 | 1/1988 | Schampes et al. | 424/DIG. 5 |
| 4,722,835 | 2/1988 | Schamper et al. | 424/DIG. 5 |
| 4,816,261 | 3/1989 | Luebbe et al. | 424/DIG. 5 |

OTHER PUBLICATIONS

Chem. Abs. of Japanese Patent No. 1066176, Mar. 1989, Nitto Chemical Co.

Primary Examiner—Dale R. Ore
Attorney, Agent, or Firm—Leonard W. Lewis; Steven J. Goldstein

[57] ABSTRACT

Antiperspirant compositions in the form of gel sticks, having acidic pH, and including an antiperspirant active, a gelling agent which comprises a dibenzylidene alditol, or mixture thereof, a hydroxy solvent for the gelling agent, and a 2-oxazolidinone derivative having a $C_1$–$C_4$ alkyl radical substituted at the 3 position of the heterocyclic ring are disclosed.

22 Claims, No Drawings

GEL STICK ANTIPERSPIRANT COMPOSITION CONTAINING 2-OXAZOLIDINONE DERIVATIVE AND PROCESS FOR MAKING THEM

TECHNICAL FIELD

The present invention relates to antiperspirant compositions the form of solid gel sticks. More particularly, the present invention relates to antiperspirant gel sticks containing dibenzylidene alditol gelling agent. The present invention further relates to a process for making the antiperspirant gel stick compositions.

BACKGROUND OF THE INVENTION

There are three main types of antiperspirant stick formulations: compressed powder sticks, gel sticks, and wax sticks. While each of these formulation types may have advantages in certain usage situations, each also has disadvantages. For example, compressed powder sticks are often brittle and hard, leaving a cosmetically-unacceptable powder on the skin upon application. Wax-based formulations can also yield cosmetically-unacceptable products due to such factors as hardness, greasiness, and stickiness. The opacity of such wax sticks and the residue created by their use may also be aesthetically undesirable.

Gel-based sticks have several advantages over both compressed powder and wax sticks. For example, the gel sticks tend to leave little or no residue or dust on the skin. Gel sticks also provide a vehicle which glides easily over the skin's surface resulting in very easy and comfortable application of the product.

Unfortunately, the formulation of antiperspirant compositions in the form of effective and stable gel sticks is difficult. One critical ingredient in antiperspirant gel sticks is the gelling agent. Many known cosmetic gel sticks comprise gelled alcoholic solutions. Gelling agents, such as sodium stearate, are commonly used to form the gel. Such gelling agents cannot be used in the presence of acidic antiperspirant active salts, due to interaction between the gelling agent, which is alkaline, and the antiperspirant active.

Gelling agents which are more useful in the preparation of antiperspirant gel sticks are the dibenzylidene alditols. For example, dibenzylidene sorbitol (DBS) is a well-known gelling agent. See, for example, U.S. Pat. No. 4,154,816, Roehl et al., issued May 15, 1979; U.S. Pat. No. 4,816,261, Luebbe et al., issued Mar. 28, 1989; and U.S. Pat. No. 4,743,444, McCall, issued May 10, 1988. Various substituted dibenzylidene alditol gelling agents have been found to be of benefit in antiperspirant gel sticks since they can exhibit improved stability in the acidic environment of the antiperspirant gel stick, and consequently improve shelf life of the product.

Japanese Published Application 64-62377, Kao, published Mar. 8, 1989, describes fluorinated dibenzylidene polyhydric alcohol derivatives which are effective gelling agents for cosmetic compositions containing a wide range of organic solvents.

U.S. Pat. No. 4,429,140, Murai et al., issued Jan. 31, 1984, discloses a method for producing DBS and its derivatives. Disclosed DBS derivatives include those where the benzene ring is substituted with from 1 to 3 lower alkyl groups, lower alkoxy groups, halogen atoms or nitro groups.

U.S. Pat. No. 4,371,645, Mahaffey, issued Feb. 1, 1983, describes plastic compositions which include DBS derivatives for improved transparency. These DBS derivatives must include a chlorine or bromine substituent in the meta and/or para positions and may also include lower alkyl, hydroxy, methoxy, mono- or dialkyl amino, or fluorine substituents. Di(para-chloro) DBS, di(para-fluoro) DBS, and di(para-methoxy) DBS are all specifically disclosed.

European Patent Application 0286522, Roquette Freres, published Dec. 1, 1988, describes a process for making high purity alditol diacetals. Para-chloro DBS is disclosed.

DBS-type compounds found to be particularly useful for antiperspirant gel sticks are disclosed in U.S. patent application Ser. No. 07/696,377, "Gel Stick Antiperspirant Compositions", Oh, Juneja, and Connor, filed on May 6, 1991, the same filing date as the present patent, and its parent application Ser. No. 07/505,807, Oh, Juneja, and Connor, filed Apr. 6, 1990 Disclosed are substituted dibenzylidene alditols that are derivatized at the meta position of the benzene rings. Exemplary compounds include di(meta-fluoro) DBS and di(meta-chloro) DBS. These meta-substituted dibenzylidene alditols have improved stability in acidic conditions.

During processing and manufacture of antiperspirant gel sticks containing dibenzylidene alditol gelling agents, it is necessary to solubilize the gelling agent in a solvent, typically a monohydric or polyhydric alcohol. In order to do this, it is necessary to heat the ingredients to a temperature which is high enough to induce solubilization and which is also above the gel point of the gelling agent/solvent solution. Unfortunately, the relatively high temperatures required tend to cause even the best dibenzylidene alditol gelling agents to degrade in the presence of the acidic antiperspirant active, or other acidic material. Accordingly, there is a need to provide antiperspirant gel stick compositions containing benzylidene alditol gelling agents that can be made at reduced processing temperatures. This can provide reduced decomposition of the dibenzylidene alditol gelling agent during processing, and provide more efficient utilization of gelling agent in the final product. The ability to farm the gels by processing at lowered processing temperatures also can reduce by-products and improve stability and processing of other ingredients typically included in antiperspirant compositions, e.g., perfumes and other volatile components, as well as improve compatibility with plastic packaging into which heated molten antiperspirant compositions may be added. There is further a need to provide a process for making such antiperspirant gel stick compositions.

Various attempts have been made in the past to meet these objects. For example, in U.S. Pat. No. 4,719,102, Randhawa et al., issued Jan. 12, 1988, it is disclosed to prepare an antiperspirant gel stick containing an acidic antiperspirant active, a dibenzylidene monosorbitol acetal gelling agent, alcohol solvent, and an organic compatible solvent of not greater than about five carbon atoms which is a good hydrogen bond donor or acceptor. Cyclic esters, amides, amines, ketones, ureas, carbamates, sulfoxides, and sulfones are discussed. More particularly, such materials as lactones, lactams, cyclic ketones, urea, cyclic carbamates, cyclic sulfoxides, cyclic sulfones, and their open chain analogs having no more than five carbon atoms are discussed. Specific examples are morpholine, pyridine, acetic acid, ethylene carbonate, propylene carbonate, N-methyl pyrrolidone, pyrrolidone, butyrolactone, dimethylsulfoxide, dimethyl formamide, 2-ethylethanol, and caprolactam. In U.S. Pat. No. 4,722,835, Schamper et al., issued Feb. 2, 1988, it is proposed to incorporate into an antiperspirant stick a small, polar organic compound in combination with the dibenzylidene monosorbitol acetal gelling agent, antiperspirant active, a basic metallic salt, and an alcohol cosolvent. The small, polar organic compound is morpholine, pyridine, acetic acid, ethylene carbonate, propylene carbonate, N-methyl pyrrolidone, pyrrolidone, butyrolactone, dimethylsulfoxide, dimethylformamide, 2-ethoxyethanol, and caprolactam. Whereas the compositions of these patents are said to be able to be processed at reduced temperatures, the exemplified solvents added to reduce processing temperature unfortunately tend to either cause off-odors in the final product, are not stable under acidic conditions, or present skin compatibility issues, such as (but not limited to) skin irritation. Thus it remains desirable, and it is an object of this invention, to provide compositions and a method of making them, which exhibit a combination of significantly reduced processing temperature requirements without incurring the disadvantages associated with prior known compositions.

It is also an object of this invention to provide compositions and a method for making them, as described above, which provide effective gels for use in antiperspirant applications, and which can provide both good antiperspirant efficacy and cosmetic characteristics.

The present invention provides antiperspirant compositions containing particular cosolvents used in combination with hydroxy solvents (such as mono- and polyhydric alcohols) in benzylidene alditol-containing antiperspirant gel stick compositions which enable the compositions to be made at reduced temperatures. Specifically, the 2-oxazolidinone compounds have a lower alkyl (e.g., $C_1$–$C_4$) substituent located at the 3 position of the heterocyclic ring. The present invention also provides a method of making such compositions, by which processing temperature can be reduced relative to processes not including the selected 2-oxazolidinone cosolvent.

The use of 2-oxazolidinone compounds as cosolvents in dibenzylidene alditol-containing gel stick compositions can lower the processing temperature required, and consequently can reduce gelling agent degradation during processing. They can also improve the gelling agent efficiency and the gel characteristics in the final product.

2-oxazolidinone compounds are disclosed for use in various applications, such as electro-chemical applications, e.g., U.S. Pat. No. 3,951,685, and Japanese Patent JP 61 55,196 (1985). They also have been disclosed, for example, as being useful as antiwear/antioxidant compounds for lubricants in electronic devices, e.g., JP 6155196 (1986), and as a topical mosquito repellent, e.g., "Topical Mosquito Repellents X: 2-Oxazolidones", A. Skinner, H. T. Crawford, D. Skidmore, and I. Maibach, *J. Pharmaceutical Sciences*, Vol. 66, No. 4, April 1977, pp 587–589. 2-Oxazolidinones are also described, for example, in "Liquid 2-Oxazolidones. 1. Dielectric Constants, Viscosities, and Other Physical Properties of Several Liquid 2-Oxazolidones", H. L. Huffman, Jr. and P. G. Sears, *J. Solution Chemistry*, Vol. 1, No. 2, 1972, pp 187–196, and as solvents, detergents, pigments, dye compositions, polymers, and chemical intermediates. Whereas patents to Schamper et al. and Randhawa et al., referenced above, very generally mention cyclic carbamates, i.e., 2-oxazolidinones, they do not disclose the 3-(alkyl)-substituted 2-oxazolidinones hereof nor suggest the necessity of the alkyl substituent at the 3 position of the heterocyclic ring for fulfilling the objects here for a stable, efficacious, and skin compatible antiperspirant gel stick.

SUMMARY OF THE INVENTION

The present invention provides for solid antiperspirant compositions in gel stick form, having acidic pHs, comprising:

(a) from about 0.5% to about 35% of an antiperspirant active;

(b) from about 0.5% to about 10% of a gelling agent selected from the group consisting of substituted and unsubstituted dibenzylidene alditols (such as sorbitols, xylitols, and ribitols), and mixtures thereof;

(c) from about 5% to about 98% of a hydroxy solvent for said gelling agent, said solvent selected from the group consisting of monohydric and polyhydric alcohols; and (d) from about 0.5% to about 40% of a 2-oxazolidinone cosolvent having a $C_1$–$C_4$ alkyl radical substituted at the 3 position of the heterocyclic ring, or a mixture thereof.

The present invention also relates to an improved process for making an antiperspirant gel stick composition, having acidic pH, containing hydroxy solvent, substituted or unsubstituted dibenzylidene alditol gelling agent, and antiperspirant active, said process comprising solubilizing said gelling agent in a heated solvent system to form a solution and subsequently cooling said solution to form a gel, wherein the improvement comprises incorporating into said solvent system a sufficient amount of 2-oxazolidinone substituted at the 3 position of the heterocyclic ring with $C_1$–$C_4$ alkyl to significantly reduce the gellation temperature of the solution.

DETAILED DESCRIPTION OF THE INVENTION

The solid antiperspirant compositions encompassed by the present invention are in the form of gel sticks. These sticks have a suitable hardness such that they deposit an effective amount of antiperspirant material on the skin during normal use, while maintaining dimensional stability upon use and storage. Hardness of sticks can be determined by a variety of methods, including American Society for Testing and Materials (ASTM) Method D-5. This method involves the use of a needle or polished cone of particular weight and dimension, which is allowed to travel downward through the stick material for a predetermined period of time. The distance travelled by the needle or cone is a relative measure of stick hardness. Using Method D-5, with an ASTM-D1321 arrowhead-type penetration needle (Model 13-401-10, sold by Fischer Scientific Co.), weighing 50 grams, and a Model 13-399-10 Penetrometer (sold by Fischer Scientific Co.), the stick compositions of the present invention preferably have an average penetration value of from about 60 to about 200, measured in units of tenths of a millimeter, more preferably from about 100 to about 160, over a period of 5 seconds at ambient temperature. These values represent an average penetration for sticks within a given production batch, since such penetration values may vary from stick to stick within the batch.

The stick compositions of the present invention, by virtue of their incorporation of antiperspirant actives, are acidic in nature. Specifically, they have an apparent pH of from about 1.5 to about 4. The term "apparent pH" is used herein since the compositions are generally non-aqueous and, therefore, the pH of the composition is being measured in a non-aqueous system. Specifically, the pH is determined by melting the stick and measuring its pH at 25° C. using a standard pH meter. If the stick is melted at a relatively high temperature (for example, about 120° C. for about 1 hour), it will not resolidify upon cooling and the pH at 25° C. can be easily measured. Under these conditions, the apparent pH of the compositions of the present invention should be from about 1.5 to about 4.

All parts, percentages and ratios specified herein are by weight, unless otherwise specified.

The required, as well as the optional, components of the present invention are described in detail below.

Gelling Agent

The compositions of the present invention include from about 0.5% to about 10%, preferably from about 2% to about 5%, most preferably from about 2% to about 3.5%, of a specifically defined gelling agent component. This gelling agent component is a dibenzylidene alditol (for example, a sorbitol, xylitol or ribitol) which can be substituted or unsubstituted. Preferred are dibenzylidene sorbitol (DBS) and DBS derivatives.

To aid in understanding the present invention, the following are diagrams of dibenzylidene sorbitol, and dibenzylidene xylitol with the ortho, meta and para positions indicated.

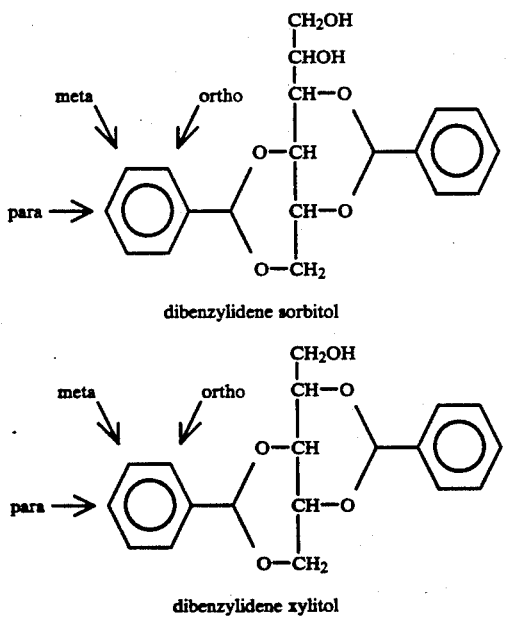

Dibenzylidene ribitol is structurally similar to dibenzylidene xylitol, except it is based on ribitol, rather than xylitol.

Other unsubstituted dibenzylidene alditols include dibenzylidene xylitol (DBX) and dibenzylidene ribitol (DBR).

The preferred substituted dibenzylidene alditols are substituted with one or more electron withdrawing groups. It is especially preferred for the substituents that are electron withdrawing groups to be located at the meta position, although substituents can also be located at the para or ortho positions. Likewise, substituents can be located at a combination of the meta and para, meta and ortho, or para and ortho positions. The preferred electron withdrawing substituents include —$CH_2F$, —$CH_2Cl$, —F, —Cl, —Br, —I, and —CH=$CHNO_2$. Preferably, at least one of the electron withdrawing substituents is located at the meta position of the benzene ring. Multiple substituents (including those not on the list) may be utilized in these preferred gelling agents as long as at least one from the list is located at the meta position. Most preferably, the alditol is sorbitol.

In other preferred gelling agents, at least one of certain substituents are located at the meta or para position of the benzene ring. Once again, more than one of these substituents (or even substituents not on the list) may be included in a particular molecule, as long as at least one from the list is positioned at the meta or para position. These substituents include:

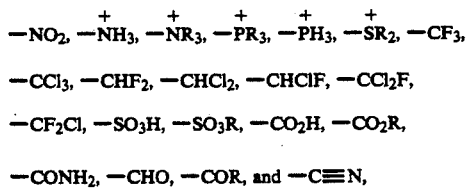

wherein R is $C_1$–$C_4$ alkyl.

Especially preferred substituted gelling agents for use in the present invention include the following substituents at the meta position: —$CH_2F$, —$CH_2Cl$, —F, —Cl, —Br, —I, and —CH=$CHNO_2$; particularly preferred are the —F and —Cl substituents. It is preferred that this meta substitution be the only substitution on the benzene ring. The substituents described herein will generally be found on both benzene rings of the compound. Particularly preferred are di(meta-fluorobenzylidene) sorbitol and di(meta-chlorobenzylidene) sorbitol.

The substituents listed above provide gelling agents which exhibit good stability in the acid environment of an antiperspirant composition. A preferred sub-group of these substituents are those which have smaller molecular sizes since they tend to generally provide stronger gels. Thus, for example, the gel provided by a fluorine or chlorine substituted compound tends to be stronger than one provided by a trifluoromethyl substituted compound. It is also preferred that the gelling agents utilized in the compositions of the present invention have a high purity. For example, they should be substantially free of para-toluene sulfonic acid or any other catalyst used in their synthesis as well as any salt forms (e.g., sodium) of these gelling agents. The presence of such impurities may tend to weaken the gel formed.

Mixtures of the gelling agents specified herein may be used in the compositions of the present invention.

Gelling agents that can be used herein are generally disclosed in British Patent 1,291,819, published Oct. 4, 1972, U.S. Pat. No. 4,518,582, Schamper et al., issued May 28, 1985, U.S. Pat. No. 4,154,816, Roehl et al., issued May 15, 1979; U.S. Pat. No. 4,816,261, Luebbe et al., issued Mar. 28, 1989; U.S. Pat. No. 4,743,444, McCall, issued May 10, 1988, and U.S. Pat. No. 4,429,140, Murai et al., issued Jan. 31, 1984, all of which are incorporated by reference herein. The preferred unsubstituted DBS is commercially available, for example, as GELL-ALL-D (manufactured by New Japan Chemical Co., Ltd.) and MILLITHIX 925 (manufactured by Milliken Chemical, Division of Milliken & Company).

The preferred meta-substituted gelling agents are generally formed by converting a meta-substituted benzaldehyde to the corresponding meta-substituted DBS using a reaction such as that taught in European Patent Application 0286522, Roquette Freres, published Dec. 1, 1988, incorporated herein by reference. As specific examples, the synthesis of meta-fluoro DBS and metachloro DBS is described below.

A solution of D-sorbitol (1006 g; 5.52 mol) in 3000 mL of distilled water, m-fluorobenzaldehyde (1240 g; 9.99 mol), and p-toluenesulfonic acid monohydrate (1310 g; 6.87 mol) is stirred at 30° C. for 21 h. The resulting suspension is neutralized to a pH of 7.0–7.5 with an aqueous 10% NaOH solution, and the white precipitate is collected by filtration. The solid is then suspended and stirred, in succession, in reagent grade acetone (3 ×10.0 L), and hot (60° C.) distilled water (3×10.0 L), collected, and dried in vacuo at 50° C. to give 1113 g (47%) of purified di(meta-fluoro) DBS.

Di(meta-chloro) DBS is synthesized using a similar procedure, except that meta-chloro benzaldehyde is used in place of metafluoro benzaldehyde.

Para-substituted compounds used in the present invention are synthesized using a similar procedure, except that para-substituted benzaldehyde is utilized as the starting material. The general method for synthesizing substituted dibenzylidene xylitols and substituted dibenzylidene ribitols is taught in Japanese Published Application 64-62377, Kao, published Mar. 8, 1989, and U.S. Pat. No. 4,429,140, Murai et al., issued Jan. 31, 1984, both incorporated herein by reference. Ortho-substituted compounds can be made in a similar manner.

ANTIPERSPIRANT ACTIVE

The compositions of the present invention also contain from about 0.5% to about 35%, preferably from about 5% to about 35%, more preferably from about 5% to about 25%, of an antiperspirant active. The antiperspirant actives hereof are antiperspirant active astringent metal salts and astringent complexes of such salts. The active may be incorporated either in solubilized or particulate form. If a clear or translucent stick composition is desired, the composition must comprise an antiperspirant active which can exist in solubilized form in the solvent system. This solvent system can essentially be the same hydroxy solvent and cosolvent used to form the base matrix with the gelling agent. Alternately, other solvents can be used as the antiperspirant active solvent. These weight percentages are calculated on an anhydrous metal salt basis (exclusive of glycine, the salts of glycine, or other complexing agents). If used in particulate form, the material preferably has a particle size of from about 1 to about 100 microns, preferably from about 1 to about 50 microns. They may be impalpable or microspherical in form and, preferably, have a high bulk density (e.g., greater than about 0.7 g/cm$^3$). Such materials include, for example, many aluminum or zirconium astringent salts or complexes and are well known in the antiperspirant art.

Any aluminum astringent antiperspirant salt or aluminum and/or zirconium astringent complex can be employed herein. Salts useful as astringent antiperspirant salts or as components of astringent complexes include aluminum halides, aluminum hydroxyhalides, zirconyl oxyhalides, zirconyl hydroxyhalides, and mixtures of these materials.

Aluminum salts of this type include aluminum chloride and the aluminum hydroxyhalides having the general formula $Al_2(OH)_xQy \cdot XH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. No. 3,887,692, Gilman, issued Jun. 3, 1975, and U.S. Pat. No. 3,904,741, Jones and Rubino, issued Sep. 9, 1975, incorporated herein by reference.

Zirconium compounds which are useful in the present invention include both the zirconium oxy salts and zirconium hydroxy salts, also referred to as the zirconyl salts and zirconyl hydroxy salts. These compounds may be represented by the following general empirical formula:

$$ZrO(OH)_{2-nz}B_z$$

wherein z may vary from about 0.9 to about 2 and need not be an integer, n is the valence of B, 2-nz is greater than or equal to 0, and B may be selected from the group consisting of halides, nitrate, sulfamate, sulfate, and mixtures thereof. Although only zirconium compounds are exemplified in this specification, it will be understood that other Group IVB metal compounds, including hafnium, can be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than 0 groups per molecule.

Several types of antiperspirant complexes utilizing the above antiperspirant salts are known in the art. For example, U.S. Pat. No. 3,792,068, Luedders et al., issued Feb. 12, 1974, discloses complexes of aluminum, zirconium and amino acids, such as glycine. Complexes such as those disclosed in the Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by
(A) co-dissolving in water
 (1) one part $Al_2(OH)_{6-m}Q_m$, wherein Q is an anion selected from the group consisting of chloride, bromide and iodide, and m is a number from about 0.8 to about 2.0;
 (2) x parts $ZrO(OH)_{2-a}Q_a \cdot nH_2O$, where Q is chloride, bromide or iodide; where a is from about 1 to about 2; where n is from about 1 to about 8; and where x has a value of from about 0.16 to about 1.2;
 (3) p parts neutral amino acid selected from the group consisting of glycine, dl-tryptophane, dl-β-phenylalanine, dl-valine, dl-methionine and β-alanine, and where p has a value of from about 0.06 to about 0.53;

(B) co-drying the resultant mixture to a friable solid; and (C) reducing the resultant dried inorganic-organic anti-perspirant complex to particulate form.

A preferred aluminum compound for preparation of such ZAG type complexes is aluminum chlorhydroxide of the empirical formula $Al_2(OH)_5Cl.2H_2O$. Preferred zirconium compounds for preparation of such ZAG-type complexes are zirconyl hydroxychloride having the empirical formula $ZrO(OH)Cl.3H_2O$ and the zirconyl hydroxyhalides of the empirical formula $ZrO(OH)_{2-a}Cl_2.nH_2O$ wherein a is from about 1.5 to about 1.87, and n is from about 1 to about 7. The preferred amino acid for preparing such ZAG-type complexes is glycine of the formula $CH_2(NH_2)COOH$. Salts of such amino acids can also be employed in the antiperspirant complexes. See U.S. Pat. No. 4,017,599, Rubino, issued Apr. 12, 1977, incorporated herein by reference.

A wide variety of other types of antiperspirant complexes are also known in the art. For example, U.S. Pat. No. 3,903,258, Siegal, issued Sep. 2, 1975, discloses a zirconium aluminum complex prepared by reacting zirconyl chloride with aluminum hydroxide and aluminum chlorhydroxide. U.S. Pat. No. 3,979,510, Rubino, issued Sep. 7, 1976, discloses an antiperspirant complex formed from certain aluminum compounds, certain zirconium compounds, and certain complex aluminum buffers. U.S. Pat. No. 3,981,896, issued Sep. 21, 1976, discloses an antiperspirant complex prepared from an aluminum polyol compound, a zirconium compound and an organic buffer. U.S. Pat. No. 3,970,748, Mecca, issued Jul. 20, 1976, discloses an aluminum chlorhydroxy glycinate complex of the approximate general formula $[Al_2(OH)_4Cl][H_2CNH_2-COOH]$. All of these patents are incorporated herein by reference.

Of all the above types of antiperspirant actives, preferred compounds include the 5/6 basic aluminum salts of the empirical formula $Al_2(OH)_5Cl.2H_2O$, such compounds being commonly referred to as aluminum chlorohydrates ("ACH"); mixtures of $AlCl_3.6H_2O$ and $Al_2(OH)_5Cl.2H_2O$ with aluminum chloride to aluminum hydroxychloride weight ratios of up to about 0.5; ZAG type complexes wherein the zirconium salt is $ZrO(OH)Cl.3H_2O$, the aluminum salt is $Al_2(OH)_5Cl.2H_2O$ or the aforementioned mixtures of $AlCl_3.6H_2O$ and $Al_2(OH)_5 Cl.2H_2O$ wherein the total metal to chloride molar ratio in the complex is less than about 1.25 and the Al:Zr molar ratio is about 3.3, and the amino acid is glycine; and ZAG-type complexes wherein the zirconium salt is $ZrO(OH)_{2-a}Cl_a.nH_2O$ wherein a is from about 1.5 to about 1.87 and n is from about 1 to about 7, the aluminum salt is $Al_2(OH)_5Cl.2H_2O$, and the amino acid is glycine.

Solubilized antiperspirant actives which may be utilized in the present invention are also well known in the art, and include the actives described above. Compositions containing solubilized antiperspirant active utilize solvents, such as monohydric or polyhydric alcohols or water, to solubilize the antiperspirant active before it is incorporated into the product. Examples of actives for such use are taught, for example, in U.S. Pat. No. 4,137,306, Rubino, issued Jan. 30, 1979, U.S. patent application Ser. No. 370,559, Smith and Ward, filed Jun. 23, 1989, and European Published Application 0295070, published Dec. 14, 1988, all of which are incorporated by reference herein. ACH is the preferred type of active for compositions containing solubilized antiperspirant active.

Examples of especially preferred actives include improved efficacy ACH (IACH) and improved efficacy ZAG (IZAG). The enhanced efficacy is due to improved molecular distribution. Such materials are described in U.S. Pat. No. 4,359,456, Gosling et al., issued Nov. 16, 1982; European Patent Application Publication No. 6,739, to Unilever Limited, published Jan. 9, 1980; European Patent Application Publication No. 183,171, to Armour Pharmaceutical Company, published Jun. 4, 1986; British Patent Specification No. 2,048,229, The Gillette Company, published Dec. 10, 1980; European Patent Application Publication No. 91,628, to Unilever PLC, published Aug. 20, 1986; British Patent Specification No. 2,144,992 to The Gillette Company, published Mar. 20, 1985; European Patent Application Publication No. 7,191, to Unilever Limited, published Jan. 23, 1980; all incorporated by reference herein in its entirety; as well as previously incorporated U.S. Ser. No. 370,559, filed Jun. 23, 1989 and European Patent No. 0295070.

Hydroxy Solvent

The compositions of the present invention include from about 5% to about 98%, preferably from about 7% to about 90%, most preferably from about 60% to about 85%, of a hydroxy solvent for the gelling agent. This solvent, in combination with the 2-oxazolidinone cosolvent, forms the base matrix of the solid stick when combined with the gelling agent. As will be appreciated by those skilled in the art, the selection of a particular hydroxy solvent will depend upon the characteristics of the stick desired. For example, the hydroxy solvent can also solubilize the antiperspirant active component in formulations having solubilized antiperspirant active material. For another example, the hydroxy solvent may be selected to provide such cosmetic benefits as emolliency when applied to the skin. Hydroxy solvents useful herein include monohydric alcohols (particularly lower monohydric alcohols), polyhydric alcohols, and mixtures thereof. Water may act as a solvent and may also be included in the compositions. Water is generally present at levels of no greater than about 5%, by weight, of the final composition.

Examples of hydroxy solvents which may be utilized in the present invention include liquid polyethylene glycols (e.g., diethylene glycol, triethylene glycol), liquid polypropylene glycols (e.g., dipropylene glycol, tripropylene glycol), liquid polypropylene polyethylene glycol copolymers, water, ethanol, n-propanol, n-butanol, t-butanol, 2-methoxyethanol, 2-ethoxyethanol, ethylene glycol, 1,2-propylene glycol, 1,3-propylene glycol, 1,4-butylene glycol, 1,2-butylene glycol, isopropanol, isobutanol, diethylene glycol monomethylether, diethylene glycol monoethylether, 1,3-butylene glycol, 2,3-butylene glycol, 2,4-dihydroxy- 2-methylpentane, trimethylene glycol, glycerine, 1,3-butane diol, 1,4-butane diol, and the like, and mixtures thereof. As used herein, polyethylene glycols, polypropylene glycols, and polypropylene polyethylene glycol copolymers include the alkyl ether derivatives of these compounds (e.g., ethyl, propyl, and butyl ether derivatives). Examples of such compounds are butyl ether derivatives of polypropylene polyethylene glycol copolymers, such as PPG-5-buteth-7.

These solvents are fully described, for example, in U.S. Pat. No. 4,518,582, Schamper et al., issued May 21, 1985, and European Published Application 107,330, Luebbe et al., published May 2, 1984, both incorporated herein by reference. The preferred solvents for use herein include liquid polyethylene glycols, liquid polypropylene glycols, liquid polypropylene polyethylene glycol copolymers, propylene glycol, 1,3-butylene glycol, and 2,4-dihydroxy-2-methylpentane (sometimes referred to as hexylene glycol), and mixtures thereof. Particularly preferred solvents include propylene glycol, dipropylene glycol, tripropylene glycol, triethylene glycol, hexylene glycol, and mixtures thereof.

Cosolvent

The compositions hereof include, as an essential ingredient, a specific cosolvent for the gelling agent. The cosolvent is a 2-oxazolidinone compound having a $C_1$–$C_4$ alkyl radical substituted at the 3 position of the heterocyclic ring, or a mixture of such compounds. This cosolvent should also be miscible with the hydroxy solvent. The gelling agent must be more soluble in the cosolvent than in the hydroxy solvent, in order for the cosolvent to depress the gellation temperature of the composition and, accordingly, reduce the temperature at which the compositions hereof can be processed. For purposes hereof, the gelling agent should be sufficiently soluble in the solvents to form a substantially clear, isotropic solution.

The 3-alkyl substituted, 2-oxazolidinone cosolvent will be generally present in the composition at a level of about 0.5% to about 40%, by weight, of the composition, preferably from about 1% to about 25%, more preferably from about 5% to about 15%.

The compositions hereof should contain a sufficient amount of the 2-oxazolidinone cosolvent to significantly reduce the gellation temperature of the solution of the solvent system (said system containing the hydroxy solvent and the 2-oxazolidinone cosolvent) and the gelling agent. This is determined relative to the gellation temperature of a solution containing the gelling agent and hydroxy solvent, but not the 2-oxazolidinone cosolvent. Gellation temperature determination methods are well known in the art. The particular method by which gellation temperature is determined is not critical, although the same method must be used throughout any gellation temperature comparison. The total level of solvent should be consistent in the comparison. A proportional decrease of hydroxy solvent(s) to compensate for the addition of cosolvent will account for this. Proportions of hydroxy solvents, relative to one another, used in hydroxy solvent mixtures should also be the same. As will be appreciated by those skilled in the art, the gelling agent must be more soluble in the cosolvent than in the hydroxy solvent for a reduction in gellation temperature to occur. As used herein, by a sufficient amount of the cosolvent to significantly reduce the gellation temperature is meant that a sufficient amount of the 2-oxazolidinone cosolvent is used such that the gellation temperature is at least about 2° C. lower than for a corresponding system without the 2-oxazolidinone cosolvent, preferably at least about 3° C., even more preferably at least about 5° C. In the most preferred cases, the temperature differential is from about 10° C. to about 30° C.

The weight ratio of the hydroxy solvent to the 2-oxazolidinone cosolvent is preferably from about 1:1 to about 50:1, more preferably from about 3:1 to about 20:1, and the weight ratio of gelling agent to the 2-oxazolidinone cosolvent is preferably from about 0.05:1 to about 2:1, more preferably from about 0.1:1 to about 1:1.

Preferred 3-alkyl-substituted 2-oxazolidinone compounds hereof have the formula:

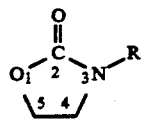

wherein the radical R at the 3 position is a $C_1$–$C_4$ alkyl, preferably a $C_1$–$C_2$ alkyl, more preferably $C_1$ (i.e., methyl).

The preferred cosolvents are 3-($C_1$–$C_4$ alkyl)-2-oxazolidinones, preferably 3-($C_1$–$C_2$ alkyl)-2-oxazolidinones. Most preferred is 3-methyl-2-oxazolidinone.

The 3-alkyl-substituted 2-oxazolidinone may also have substituents located at the 4 and 5 positions of the heterocyclic ring instead of hydrogen. Preferably, if used, such substituents are lower alkyls, e.g., $C_1$–$C_4$ alkyl, preferably $C_1$–$C_2$ alkyl, more preferably methyl. Other substituents can be present which do not cause the compound to be immiscible with the hydroxy solvent or reduce solubility of the gelling agent in it to less than the hydroxy solvent. Also, the compound should remain stable against decomposition in the processing of, and under the typical storage and use conditions of, the gel stick compositions.

The 3-alkyl substituted, 2-oxazolidinone cosolvents hereof can be made according to processes known in the art. Exemplary processes are disclosed in U.S. Pat. No. 2,755,286, Bell et al., issued Jul. 17, 1956, U.S. Pat. No. 2,399,118, Hofmeyer, issued Apr. 23, 1946, and previously referenced "Liquid 2-Oxazolidones. 1. Dielectric Constants, Viscosities, and Other Physical properties of Several Liquid 2-Oxazolidones", by Huffman and Sears, *J. of Solution Chemistry*, Vol. 1, No. 2, 1972, pp 187–196. 3 Methyl-2-oxazolidinone is commercially available, for example, from Raylo Chemicals, a division of Terochem Laboratories, Ltd (Edmonton, Alberta, Canada), and from Aldrich Chemical Co. (Milwaukee, Wis. USA).

Optional Components

The compositions of the present invention may also contain optional components which modify the physical characteristics of the compositions or serve as "active" components when deposited on the skin in addition to the antiperspirant material. Optional components useful herein are described in the following documents, all incorporated by reference herein: U.S. Pat. No. 4,049,792, Elsnau, issued Sep. 20, 1977; Canadian Patent 1,164,347, Beckmeyer et al., issued Mar. 27, 1984; European Patent Application 117,070, May, published August 29, 1984; and Geria, "Formulation of Stick Antiperspirants and Deodorants", *Cosmetics & Toiletries*, 99:55–60 (1984).

The specific non-active components that may be useful will depend upon the characteristics desired for the particular stick composition. Such components include, for example, emollients, humectants, hardeners (e.g., wax), fillers and particulate materials, colorants, perfumes, and emulsifiers. As used herein, "particulate materials" are those materials, including colloidal dispersions, that neither dissolve in the composition components nor melt during the manufacture of the stick.

The compositions of the present invention may contain from about 1% to about 40% of one or more emollients. These emollients may have an intermediate polarity, such as the ethyl, isopropyl and n-butyl diesters of adipic, phthalic and sebacic acids. Preferred examples of such emollients include di-n-butyl phthalate, diethyl sebacate, diisopropyl adipate and ethyl carbomethyl phthalate, all of which are disclosed in U.S. Pat. No. 4,045,548, Luedders et al., issued August 30, 1977, which is incorporated by reference herein. Other useful emollients include $C_{12}$-$C_{15}$ alcohol benzoates (commercially available as Finsolv from Finetex, Inc.). Useful emollients also include fatty alcohols, such as cetyl and stearyl alcohols, which (if used) will preferably be present at a level of from about 1% to about 10%, more preferably from about 1% to about 5%. The compositions of the present invention may also include non-polar emollients, such as volatile silicone oils, non-polar non-volatile emollients, and mixtures thereof. The term "volatile", as used herein, refers to those materials which have a measurable vapor pressure at ambient temperature.

Volatile silicone oils useful in the cosmetic stick compositions of the present invention are preferably cyclic or linear polydimethylsiloxanes containing from about 3 to about 9, preferably from about 4 to about 5, silicon atoms. The following formula illustrates cyclic volatile polydimethylsiloxanes useful in the antiperspirant stick compositions disclosed herein:

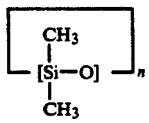

wherein n equals about 3 to about 7. Linear polydimethylsiloxanes contain from about 3 to about 9 silicon atoms per molecule and have the following general formula:

wherein n equals about 1 to about 7. Linear volatile silicone materials generally have viscosities of less than about 5 centistokes at 25° C., while cyclic materials typically have viscosities of less than about 10 centistokes. A description of various volatile silicone oils is found in Todd et al., "Volatile Silicone Fluids for Cosmetics", *Cosmetic & Toiletries*, 91, pages 27-32 (1976), the disclosures of which are incorporated by reference herein.

Examples of preferred volatile silicone oils useful herein include: Dow Corning 344, Dow Corning 345, and Dow Corning 200 (manufactured by Dow Corning Corp.); Silicone 7207 and Silicone 7158 (manufactured by Union Carbide Corp.); SF 1202 (manufactured by General Electric); and SWS-03314 (manufactured by SWS Silicones, Inc.).

Non-volatile silicone oils useful as emollient materials include polyalkylsiloxanes, polyarylsiloxanes and polyethersiloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 2 to about 400 centistokes at 25° C. Such polyalkyl siloxanes include the Viscasil series (sold by General Electric Company) and the Dow Corning 200 series (sold by Dow Corning Corp.). Polyalkylaryl siloxanes include polymethylphenyl siloxanes having viscosities of from about 15 to about 65 centistokes at 25° C. These are available, for example, as SF 1075 methylphenyl fluid (sold by General Electric Company) and 556 Cosmetic Grade Fluid (sold by Dow Corning Corp.). Useful polyether siloxane copolymers include, for example, a polyoxyalkylene ether copolymer having a viscosity of about 1200 to 1500 centistokes at 25° C. Such a fluid is available as SFI066 organosilicone surfactant (sold by General Electric Company). Polysiloxane ethylene glycol ether copolymers are preferred copolymers for use in the present compositions.

The compositions of the present invention may include a stabilizing agent which acts to stabilize the composition (especially the gelling agent) during the high temperature steps of the manufacturing process, during storage of the product, or both. These materials are generally used at levels of about 0.05% to about 5% of the composition. Examples of these material include zinc acetate, methenamine, magnesium acetate, calcium acetate, triethanolamine, diethanolamine, and mixtures thereof. Preferred stabilizing agents are salts of $C_4$-$C_6$ (saturated) dicarboxylic, $C_6$-$C_8$ (saturated) monocarboxylic, and substituted and unsubstituted benzoic acids. These will be added as salts which are at least partially soluble in the solvent system. Suitable salt-forming cations include sodium, potassium, lithium, magnesium, calcium, and zinc. Preferred salt-forming cations are sodium, potassium, magnesium, and calcium, especially sodium. Especially preferred stabilizing agents include the benzoates, succinate, and octanoate salts such as disodium succinate, sodium benzoate, and sodium octanoate.

The compositions of the present invention may also contain from about 0.5% to about 10% of an inert filler material. Suitable filler materials include colloidal silica (such as Cab-O-Sil, sold by Cabot Corp.), clays (such as bentonite), hydrophobic (quaternized) clays, silica/alumina thickeners, silicate powders such as talc, alumina silicate, and magnesium silicate, modified corn starches, metallic stearates, and mixtures thereof. The use of such fillers as stabilizing agents in cosmetic sticks is disclosed in U.S. Pat. No. 4,126,679, Davy et al., issued Nov. 21, 1987, incorporated herein by reference. The compositions of the present invention may also include perfumes, emulsifiers and coloring agents well known in the art, at levels of from about 0.1% to about 5%.

In addition to the antiperspirant actives, discussed above, the antiperspirant sticks of the present invention may also contain a safe and effective amount of one or more additional components which are meant to be deposited upon human tissue. Such active components include astringents, bacteriostats, fungistats, pigments, dyes, colorants, perfumes, emollients, ultraviolet absorbers, and mixtures thereof. These components must be stable in the formulation of the instant invention. A "safe and effective" amount of such active components is that amount which yields the desired benefit at a reasonable benefit/risk ratio for human usage. Various active components among those useful in the present invention are described in U.S. Pat. No. 4,226,889, Yuhas, issued Oct. 7, 1980, incorporated by reference herein.

The present invention further relates to a process for making an antiperspirant gel stick composition utilizing a dibenzylidene alditol gelling agent, 2-oxazolidinone substituted at the 3 position with a $C_1$-$C_4$ alkyl as a cosolvent along with a hydroxy solvent and the antiperspirant active.

The process utilizes a sufficient amount of the 2-oxazolidinone cosolvent to significantly reduce the gellation temperature of the solution. This is determined relative to the gellation temperature of a solution containing the gelling agent and hydroxy solvent, but not the 2-oxazolidinone cosolvent, as described above.

The preferred components and levels are described in more detail above. Thus, the invention also relates to an improved process for making an antiperspirant gel stick, having acidic pH, composition containing hydroxy solvent, substituted or unsubstituted dibenzylidene alditol gelling agent, and antiperspirant active, said process comprising solubilizing said gelling agent in a heated solvent to form a solution and subsequently cooling said solution to form a gel, wherein the improvement comprises incorporating into said solvent system a sufficient amount of 2-oxazolidinone substituted at the 3 position of the heterocyclic ring with $C_1$-$C_4$ alkyl to significantly reduce the gellation temperature of the solution.

In a preferred process, the antiperspirant gel stick compositions are made according to the steps of:

(a) preparing a solution containing a hydroxy solvent, a substituted or unsubstituted dibenzylidene alditol gelling agent, and a 2-oxazolidinone having a $C_1$-$C_4$ alkyl radical, or mixture thereof, substituted at the 3 position of the heterocyclic ring, wherein said gelling agent is soluble in said 2-oxazolidinone and said composition preferably has a weight ratio of said hydroxy solvent to said 2-oxazolidinone of from about 1:1 to about 50:1, and a weight ratio of said gelling agent to said 2-oxazolidinone of from about 0.05:1 to about 0.1:1;

(b) mixing an antiperspirant active into said solution; and (c) cooling said solution to ambient temperature; wherein said composition has an average penetration value of from about 60 to about 200 tenths of a millimeter at ambient temperature.

The preferred levels of the hydroxy solvent, cosolvent, gelling agent, and antiperspirant active in the final composition are as described above.

Consistent with the above, the compositions of this invention may be made by methods known to those skilled in the art. Such methods are described in "Gels and Sticks Formulary", *Cosmetics & Toiletries*, 99, 77-84 (1984), incorporated by reference herein. After the antiperspirant active and optional components are added, the solution is poured into stick molds. A solid gel forms upon cooling. As the stick composition may solidify rapidly upon cooling, care should be taken so as to maintain an elevated temperature while mixing and processing the composition.

The gel form antiperspirant stick compositions of the present invention are used in a conventional manner. Specifically, the compositions may be used to prevent and/or control perspiration wetness by topically applying, one or more times a day, an effective amount of the composition to areas of the body particularly prone to perspiration (e.g., the underarm or axillary area).

The following non-limiting examples illustrate the compositions, methods of making, and methods of use described in the present application.

EXAMPLES I–III

Opaque antiperspirant gel stick compositions are exemplified in these examples. The compositions are made according to the following procedure.

Phase A—If applicable, weigh the water into a beaker, add the sodium benzoate, and agitate at room temperature until the sodium benzoate is dissolved, to form a sodium benzoate solution.

Add the sodium benzoate solution (if any), the Phase A portion of the hydroxy solvent, and 3-methyl-2-oxazolidinone (3M20) into a 3-neck round bottom flask equipped with a reflux condenser, thermometer, and magnetic stir bar. Place the flask in a heating mantle connected to a rheostat.

Weigh the gelling agent and add it to the flask. Heat the flask while stirring until the gelling agent is completely dissolved at about 110° C. to about 132° C. for Example I, about 100° C. to about 122° C. for Example II, and about 90° C. to about 110° C. for Example III. Hold within the temperature range with stirring. Phase B—Weigh the Phase B portion of the dipropylene glycol and the ethanol (if applicable) into a round bottom flask equipped with a reflux condenser, thermometer, and mechanical stirrer. Add the antiperspirant active and mix until well dispersed. Mixing can alternately be performed with a high shear mixer. Add the fumed silica and, if applicable, the fumed aluminum oxide or diethyl sebacate, to the flask, place the flask in a heating mantle connected to a rheostat, and heat the flask to about 65° C. to about 90° C. while stirring. Hold at about 65° C. to about 90° C. for Example I, at about 55° C. to about 80° C. for Example II, and about 45° C. to about 70° C. for Example III, with stirring.

Add Phase B to Phase A flask and mix until homogenous. Cool to near, but above, gellation temperature, to avoid premature gelling, e.g., about 5° to about 10° C. above gellation temperature, determined at the point that the gelling agent visibly (with the naked eye) begins to come out of solution, i.e., begins to gel. For Example gellation temperature will typically be about 12°-15° C. below that which would be expected in a similar composition without the 3M20 (based upon a proportional increase in the hydroxy solvent(s) to replace the 3M20). For Example II, gellation temperature will typically be about 18°-21° C. lower than without 3M20. For Example III, gellation temperature will typically be about 7°-10° C. lower than without 3M20. Thus, the compositions can be processed and held during processing prior to gellation at reduced temperatures to thereby reduce decomposition of the gelling agent and improve gel stick properties. A practical benefit of this, for example, is that reduced gelling agent decomposition can be obtained while the pre-gelled product is being held in bulk during packaging (e.g., sequential pouring of the product into cannisters for subsequent cooling below gellation temperature).

| Ingredients | Examples (wt. %) | | |
| --- | --- | --- | --- |
| | I | II | III |
| Phase A | | | |
| Sodium Benzoate | 1.00 | — | 1.00 |
| Water | 2.00 | — | 2.00 |
| Hydroxy Solvent | | | |

-continued

| Ingredients | Examples (wt. %) | | |
|---|---|---|---|
| | I | II | III |
| Dipropylene Glycol | 15.00 | — | 42.50 |
| Propylene Glycol | 15.00 | 31.00 | — |
| 3-Methyl-2-Oxazolidinone (3M2O) | 10.00 | 15.00 | 5.00 |
| Di(m-fluorobenzylidene) Sorbitol | 3.00 | 3.00 | — |
| Dibenzylidene Sorbitol (unsubstituted) | — | — | 3.50 |
| Phase B | | | |
| Hydroxy Solvent | | | |
| Dipropylene Glycol | 27.00 | 30.00 | 20.00 |
| Ethanol | 10.00 | — | 10.00 |
| Zirconium Aluminum Trichlorohydrex Gly (ZAG)* | 15.00 | 15.00 | 15.00 |
| Fumed Silica** | 1.67 | 1.00 | 1.00 |
| Fumed Aluminum Oxide*** | 0.30 | — | — |
| Diethyl Sebacate | — | 5.0 | — |

*Available as WESTCHLOR ZR 30B DM Powder from Westwood Chemical Corp. (Middletown, NY, USA).
**Available as CABOSIL from Cabot Corp. (Tuscola, IL, USA).
***Available as Aluminum Oxide C from Degussa, Inc. (Teterboro, NJ, USA).

The opaque gel sticks exhibit excellent gel properties and can provide excellent antiperspirant efficacy when applied to the axillary area.

EXAMPLES IV-VI

Clear antiperspirant gel stick compositions are exemplified in these examples. The compositions are made according to the following procedure.

Phase A—If applicable, weigh the Phase A portion of the water into a beaker. Add the sodium benzoate and agitate at room temperature until the sodium benzoate is dissolved, to form a sodium benzoate solution. Add the sodium benzoate solution (if applicable), the Phase A portion of hydroxy solvent, diethyl sebacate, and the 3-methyl-2-oxazolidinone into a 3-neck round bottom flask equipped with a reflux condenser, thermometer, and magnetic stir bar. Place the flask in a heating mantle connected to a rheostat.

Weigh the gelling agent and add it to the flask. Heat the flask while stirring until the gelling agent is completely dissolved at about 110° C. to about 132° C. for Example IV, at about 100° C. to about 122° C. for Example V, and at about 90° C. to about 110° C. for Example VI. Hold within this range with stirring.

Phase B—Weigh the propylene glycol into a flask. Add the antiperspirant active and mix until homogenous. Add the Phase B portion of the water. Mix with a high energy mixer and heat to about 45° C. to about 85° C. while mixing until the active is solubilized. Deaerate.

Add solubilized active and, if applicable, the ethanol and silica into a round bottom flask equipped with a reflux condenser, thermometer, and magnetic stir bar. Place the flask in a heating mantle connected to a rheostat, and heat the flask to about 65° C. to about 90° C. for Example IV, to about 55° C. to about 80° C. for Example I, and to about 45° C. to about 70° C. for Example VI, while stirring. Hold within the applicable range with stirring.

Add Phase B to Phase A flask and mix until homogenous. Cool to near, but above, gellation temperature, to avoid premature gelling, e.g., about 5° to about 10° C. above gellation temperature, determined at the point that the gelling agent visibly (with the naked eye) begins to come out of solution, i.e., gel. For Example IV, gellation temperature will typically be about 12°-15° C. below that which would be expected in a similar composition without the 3M20 (based upon a proportional increase in the hydroxy solvent(s) to replace the 3M20). For Example V, gellation temperature will typically be about 12°-15° C. lower than without 3M20. For Example VI, gellation temperature will typically be about 7°-10° C. lower than without 3M20. Thus, the compositions can be processed and held during processing prior to gellation at reduced temperatures to thereby reduce decomposition of the gelling agent and improve gel stick properties. A practical benefit of this, for example, is that reduced gelling agent decomposition can be obtained while the pre-gelled product is being held in bulk during packaging (e.g., sequential pouring of the product into cannisters for subsequent cooling below gellation temperature).

| Ingredients | Examples (Weight %) | | |
|---|---|---|---|
| | IV | V | VI |
| Phase A | | | |
| Sodium Benzoate | 1.00 | — | 1.00 |
| Water | 2.00 | — | 2.00 |
| Hydroxy Solvent | | | |
| Dipropylene Glycol | 43.00 | — | 47.50 |
| Propylene Glycol | — | 47.00 | — |
| 3-Methyl-2-Oxazolidone (3M2O) | 10.00 | 15.00 | 5.00 |
| Diethyl Sebacate | — | 5.00 | — |
| Di(m-fluorobenzylidene) Sorbitol | 3.00 | 3.00 | — |
| Dibenzylidene Sorbitol (unsubstituted) | — | — | 3.50 |
| Phase B | | | |
| Hydroxy Solvent | | | |
| Ethanol | 10.00 | — | 10.00 |
| Propylene Glycol | 15.00 | 15.00 | 15.00 |
| Aluminum Chlorohydrate* | 13.50 | 13.50 | 13.50 |
| Fumed Silica** | 1.00 | — | 1.00 |
| Water | 1.50 | 1.50 | 1.50 |

*Available as WESTCHLOR DM 200 Powder from Westwood Chemical Corp. (Middletown, NY, USA).
**Available as CABOSIL from Cabot Corp. (Tuscola, IL, USA).

The sticks have excellent gel properties and can provide excellent antiperspirant efficacy when applied to the axillary area. The composition will be clear or translucent.

What is claimed is:

1. A solid antiperspirant composition in gel stick form, having an acidic pH, comprising:
   (a) from about 0.5% to about 35% of an antiperspirant active;
   (b) from about 0.5% to about 10% of a gelling agent selected from the group consisting of substituted and unsubstituted dibenzylidene alditols, and mixtures thereof;
   (c) from about 5% to about 98% of a hydroxy solvent for said gelling agent selected from the group consisting of monohydric and polyhydric alcohols; and
   (d) from about 0.5% to about 40% of a 2-oxazolidinone having a $C_1$–$C_4$ alkyl radical substituted at the 3 position of the heterocyclic ring, or a mixture thereof, wherein said gelling agent is more soluble in said 2-oxazolidinone than in said hydroxy solvent.

2. A solid antiperspirant composition according to claim 1 wherein said composition has a weight ratio of said hydroxy solvent to said 2-oxazolidinone of from about 1:1 to about 50:1, and a weight ratio of said gelling agent to said 2-oxazolidinone of from about 0.05:1 to about 2:1.

3. A solid antiperspirant composition according to claim 2, wherein said 2-oxazolidinone compound is a 3-($C_1$–$C_4$ alkyl)-2-oxazolidinone, or a mixture thereof.

4. A solid antiperspirant composition according to claim 3, wherein said 2-oxazolidinone compound is 3-methyl-2-oxazolidinone.

5. A solid antiperspirant composition according to claim 3, wherein the weight ratio of said hydroxy solvent to said 2-oxazolidinone is from about 3:1 to about 20:1 and the weight ratio of said gelling agent to said 2-oxazolidinone is from about 0.1:1 to about 1:1.

6. A solid antiperspirant composition according to claim 5, comprising from about 7% to about 90% of said hydroxy solvent, from about 1% to about 25% of said 2-oxazolidinone, and from about 2% to about 5% of said gelling agent.

7. A solid antiperspirant composition according to claim 4, wherein the weight ratio of said hydroxy solvent to said 2-oxazolidinone is from about 3:1 to about 20:1 and the weight ratio of said gelling agent to said oxazolidinone is from about 0.1:1 to about 1:1.

8. A solid antiperspirant composition according to claim 7, comprising from about 7% to about 90% of said hydroxy solvent, from about 1% to about 25% of said 2-oxazolidinone, and from about 2% to about 5% of said gelling agent.

9. A solid antiperspirant composition according to claim 8, comprising from about 60% to about 85% of said hydroxy solvent and from about 5% to about 15% of said 2-oxazolidinone.

10. A solid antiperspirant composition according to claim 1 wherein substituted and unsubstituted dibenzylidene alditol is selected from the group consisting of substituted or unsubstituted dibenzylidene sorbitols, substituted or unsubstituted dibenzylidene xylitols, substituted or unsubstituted dibenzylidene ribitols, and mixtures thereof.

11. A solid antiperspirant composition according to claim 4 wherein the gelling agent is a substituted or unsubstituted dibenzylidene sorbitol, or a mixture thereof.

12. A solid antiperspirant composition according to claim 11 wherein the gelling agent is di(meta-fluorobenzylidene) sorbitol, di(meta-chlorobenzylidene) sorbitol, unsubstituted dibenzylidene sorbitol, or a mixture thereof.

13. A solid antiperspirant composition according to claim 1 wherein the hydroxy solvent is selected from the group consisting of liquid polyethylene glycols, liquid polypropylene glycols, liquid polyethylene polypropylene glycol copolymers, ethanol, n-propanol, n-butanol, t-butanol, 2-methoxyethanol, 2-ethoxyethanol, ethylene glycol, 1,2-propylene glycol, 1,3-propylene glycol, 1,4-butylene glycol, 1,2-butylene glycol, isopropanol, isobutanol, diethylene glycol monomethylether, diethylene glycol monoethylether, 1,3-butylene glycol, 2,3-butylene glycol, 2,4-dihydroxy-2-methylpentane, trimethylene glycol, triethylene glycol, glycerine, 1,3-butane diol, 1,4-butane diol, and mixtures thereof.

14. A solid antiperspirant composition according to claim 13 wherein the solvent is selected from the group consisting of triethylene glycol, propylene glycol, dipropylene glycol, tripropylene glycol, hexylene glycol, and mixtures thereof.

15. A solid antiperspirant composition according to claim 1 wherein the antiperspirant active is in solubilized form.

16. A solid antiperspirant composition according to claim 1 wherein the antiperspirant active is in particulate form.

17. A solid antiperspirant composition in gel stick form, having an acidic pH, comprising:
(a) from about 5% to about 35% of an antiperspirant active;
(b) from about 2% to about 5% of a gelling agent selected from the group consisting of substituted and unsubstituted dibenzylidene sorbitols;
(c) from about 60% to about 85% of a hydroxy solvent selected from the group consisting of monohydric and polyhydric alcohols, and mixtures; thereof; and
(d) from about 5% to about 15% of a cosolvent selected from the group consisting of 3-($C_1$-$C_4$) methyl-2-oxazolidinones;

wherein said gelling agent is more soluble in said cosolvent than in said hydroxy solvent.

18. A method for preventing and controlling perspiration wetness in humans comprising the application to the underarm area of an effective amount of the solid antiperspirant composition according to claim 1.

19. A process for making an antiperspirant gel stick composition, having acidic pH, containing hydroxy solvent, substituted or unsubstituted dibenzylidene alditol gelling agent, and antiperspirant active, said process including the steps of solubilizing said gelling agent in a heated solvent and subsequently cooling said solution to form a gel, wherein the improvement comprises incorporating into said solvent system a sufficient amount of 2-oxazolidinone substituted at the 3 position of the heterocyclic ring with $C_1$-$C_4$ alkyl to significantly reduce the gellation temperature of the solution.

20. A process for making an antiperspirant gel stick composition, said composition having acidic pH, comprising:
(a) preparing a solution containing an alcoholic solvent, a substituted or unsubstituted dibenzylidene alditol gelling agent and a 2-oxazolidinone having a $C_1$-$C_4$ alkyl radical substituted at the 3 position of the heterocyclic ring, or a mixture thereof, wherein said gelling agent is more soluble in said 2-oxazolidinone than in said hydroxy solvent, and said composition has a weight ratio of said alcoholic solvent to said 2-oxazolidinone of from about 1:1 to about 50:1, and a weight ratio of said gelling agent to said 2-oxazolidinone of from about 0.05:1 to about 2:1;
(b) mixing an astringent antiperspirant active into said solution; and
(c) cooling said solution to ambient temperature; wherein said composition has an average penetration value of from about 60 to about 200 tenths of a millimeter at ambient temperature.

21. The product made according to the process of claim 19.

22. The product made according to the process of claim 20.

* * * * *